United States Patent
Park et al.

(10) Patent No.: US 6,964,952 B2
(45) Date of Patent: Nov. 15, 2005

(54) THERAPEUTIC COMPOSITION FOR BROAD SPECTRUM DERMAL DISEASE

(75) Inventors: Chang Seo Park, Gwacheon-si (KR); Jin Wook Kim, Yougin-si (KR); Jin Hee Choi, Seoul (KR); Ui Chan Koh, Seoul (KR)

(73) Assignee: Doosan Corporation (KR)

( * ) Notice: Subject to any disclaimer, the term of this patent is extended or adjusted under 35 U.S.C. 154(b) by 34 days.

(21) Appl. No.: 10/662,002

(22) Filed: Sep. 12, 2003

(65) Prior Publication Data

US 2004/0138177 A1 Jul. 15, 2004

Related U.S. Application Data

(63) Continuation of application No. PCT/KR02/00428, filed on Mar. 12, 2002.

(30) Foreign Application Priority Data

Mar. 12, 2001 (KR) ........................................ 2001-12591

(51) Int. Cl.$^7$ ............................................. A61K 31/66
(52) U.S. Cl. ....................... 514/110; 514/120; 514/141; 514/880; 514/882
(58) Field of Search ................................ 514/110, 120, 514/141, 880, 882

(56) References Cited

U.S. PATENT DOCUMENTS

| | | | |
|---|---|---|---|
| 5,565,439 A | * 10/1996 | Piazza et al. | 514/110 |
| 5,578,641 A | 11/1996 | Jackson et al. | |
| 5,958,742 A | 9/1999 | Park et al. | |
| 6,348,201 B2 | * 2/2002 | Murata et al. | 424/401 |

FOREIGN PATENT DOCUMENTS

WO    WO 02/072082 A1    3/2002

* cited by examiner

*Primary Examiner*—Vickie Kim
(74) *Attorney, Agent, or Firm*—Knobbe Martens Olson & Bear, LLP

(57) ABSTRACT

The invention relates to a therapeutic composition for broad spectrum dermal disease and in particular, to a composition comprising principal lipid components of skin, preferably having about 30 to 90% by weight of a carrier for applying to skin; 0.01 to 5.0% by weight of sphingolipid long-chain base; 0.001 to 1.0% by weight of lysophosphatidic acid; and 1 to 40% by weight of organic or inorganic additives. The composition is useful for the treatment and improvement of atopic dermatitis, psoriasis, acne, ichthyosis, infectious dermatitis, pruritus, erythema derived from pruritus, vulnus, chapping of skin and ulcer, etc.

7 Claims, 6 Drawing Sheets

THERAPEUTIC COMPOSITION FOR BROAD SPECTRUM DERMAL DISEASE

RELATED APPLICATIONS

This application is a continuation of International Application No. PCT/KR02/00428, filed Mar. 12, 2002, which claims priority to Korean Patent Application No. KR 2001-12591, filed Mar. 12, 2001, the disclosures of which are incorporated by reference herein in their entireties.

BACKGROUND OF THE INVENTION

1. Field of the Invention

The present invention relates to a pharmaceutical composition which can be employed as an essential therapeutic agent for dermal disease caused by damage of a skin barrier, such as atopic dermatitis, and specifically, it concerns a composition which repair a damaged skin barrier to a normal condition so as to recover the skin's properties of moisture-retaining capacity and selective permeability, thereby maximizing inhibition or alleviation of skin irritation due to external irritants. More particularly, the invention relates to a therapeutic composition for a broad spectrum of skin diseases, comprising sphingolipid long-chain base selected from the group consisting of phytosphingosine, acetylphytosphingosine, tetraacetyl phytosphingosine, hexanoylphytosphingosine and acetylphytosphingosine phosphate, andlysophosphatidic acid selected from the group consisting of lyso-stearoyl phosphatidic acid (18:0), lyso-oleoyl phosphatidic acid (18:1), lyso-palmitoyl phosphatidic acid (16:0) and natural lyso-phosphatidic acid derived from egg yolk or beans, with respect to the total weight of the composition.

2. Description of the Related Art

Many skin diseases such as psoriasis and atopic dermatitis are known to be diseases which are hard to cure, like cancers, AIDS and dementia, and thereby plague the human race. The reasons for these diseases are still not clearly understood, and a fundamental therapy is not yet developed. It is believed that a combination of multiple factors including genetic, environmental and immunological causes, may cause skin diseases. Such diseases have characteristics of chronic and periodic onset and recurrence.

Although most skin diseases are not fatal, many patients experience severe hindrance in managing daily lives, and especially, juveniles including children have difficulties in doing school work, due to emotional upset and loss of concentration, causing social problems. Regarding atopic dermatitis, it was reported that 85 percent of patients became ill before the age of 5, and 60% of the patients still have symptoms of atopic dermatitis when they reach adulthood. Though it is known that on average, 5 to 10% of the total population experiences this disease, and the incidence is increasing due to environmental causes. One study found that the number of such patients in the United States increased by three times since the 1970s. In the world, Korea belongs to a group of nations whose incidence of patients with atopic dermatitis is high. The reason for this is thought to be the trend that apartments are becoming the primary accommodation. According to a survey of the United States, 56% of the respondents said they feel uncomfortable in their social lives, and 80% suffer sleep difficulties.

So far, there is no perfect cure for atopic dermatitis. Some antibiotics have been used for the treatment of skin infections which often accompany atopic dermatitis, depending on the progress of the lesions. UV radiation or immunosuppressants can also be applied to the patients with severe lesions. Such treatments are based on the knowledge that abnormal functioning of macrophages and T cells is a main factor of atopic dermatitis, and overproduction of IL-4 and IL-5 in the skin tissues of the lesions are closely related to high concentrations of IgE and eosinophilia which are characteristics of atopic dermatitis (Ohmen J D et al., *J Immunol.*, 154: 1956–1963, 1995-Overproduction of IL-10; Hamid Q et al., *J Clin. Invest.*, 94: 870–876, 1994-Cytokine expression; which are incorporated by reference herein in their entireties).

Steroid-containing ointments or anti-histamine agents have been used, but are only a partial cure, and have considerable side effects. Dermatologists warn patients about side effects caused by long-term steroid therapy, and it is observed that termination of the application of steroids is often followed by lesion recurrence. Steroids for external or oral application make the skin layers thin or cause osteoporosis and inhibit growth in children, upon long-term use. Therefore, much research conducted so far focuses on development of steroid substances with fewer side effects. Studies on non-steroid or low steroid preparations were presented at the American Academy of Dermatology Annual Conference in 2000, thus being a recent trend.

Considering the above, what is needed is a composition for dermatological application which is effective in treating skin disorders, yet has fewer side effects that the above described treatments.

SUMMARY OF THE INVENTION

Therefore, the present invention has been made in view of the above problems, and is directed to a therapeutic composition for a broad spectrum of skin diseases. In some aspects of the invention, the composition comprises sphingolipid long-chain base, including phytosphingosine and its derivatives and serve as one constituent of lipids in the skin, and, functional phospholipid such as lysophosphatidic acid.

In some aspects of the invention, a therapeutic composition for treatment of skin diseases is provided, having a sphingolipid long-chain base and lysophosphatidic acid. In some embodiments, the sphingolipid long-chain base can be present at a percentage (by weight) from about 0.01 to 5.0%. In some embodiments, the lysophosphatidic acid can be present at from about 0.001 to 1.0%. The sphingolipid long-chain base can be, for example, phytosphingosine, acetylphytosphingosine, tetraacetyl phytosphingosine, hexanoylphytosphingosine, or acetylphytosphingosine phosphate.

In accordance with another aspect of the present invention, the above and other objects can be accomplished by the provision of a therapeutic composition for a broad spectrum of skin diseases, comprising 30 to 90% by weight of a conventional substrate or a carrier for topical application; 0.01 to 5% by weight of sphingolipid long-chain base; 0.001 to 1% by weight of lysophosphatidic acid; and 1 to 40% by weight of organic or inorganic additives.

Preferably, the sphingolipid long-chain base is one or more selected from the group consisting of phytosphingosine, acetylphytosphingosine, tetraacetyl phytosphingosine, hexanoylphytosphingosine and acetylphytosphingosine phosphate It is preferable that the organic additives may contain ceramide, cholesterol and fatty acid at a weight ratio of 40 to 60%:20 to 30%:20 to 30%, pursuant to the composition of normal skin.

In some embodiments, ceramide used herein may include ceramide 3, ceramide 6, and a mixture thereof, and its stereochemical composition is the same as in skin lipids.

In some embodiments, the lysophosphatidic acid used herein may be selected from the group consisting of lyso-stearoyl phosphatidic acid (18:0), lyso-oleoyl phosphatidic acid (18:1), lyso-palmitoyl phosphatidic acid (16:0) and natural lyso-phosphatidic acid derived from egg yolk or beans.

In accordance with another aspect of the present invention, there is provided a therapeutic composition for a broad spectrum of skin diseases, including atopic dermatitis, eczema, psoriasis with hyperkeratosis, skin inflammation, pruritus, bacterial infection, acne, and wounds.

In accordance with yet another aspect of the present invention, there is provided a therapeutic composition for a broad spectrum of skin diseases, formulated by using conventional carriers for skin in the form of cream, lotion, skin toner, essence, body wash, and shampoo.

BRIEF DESCRIPTION OF THE DRAWINGS

The above and other objects, features and other advantages of the present invention will be more clearly understood from the following detailed description taken in conjunction with the accompanying drawings, in which:

FIG. 2 displays microscopic images of skin tissues.

DETAILED DESCRIPTION OF THE INVENTION

Figure 1:
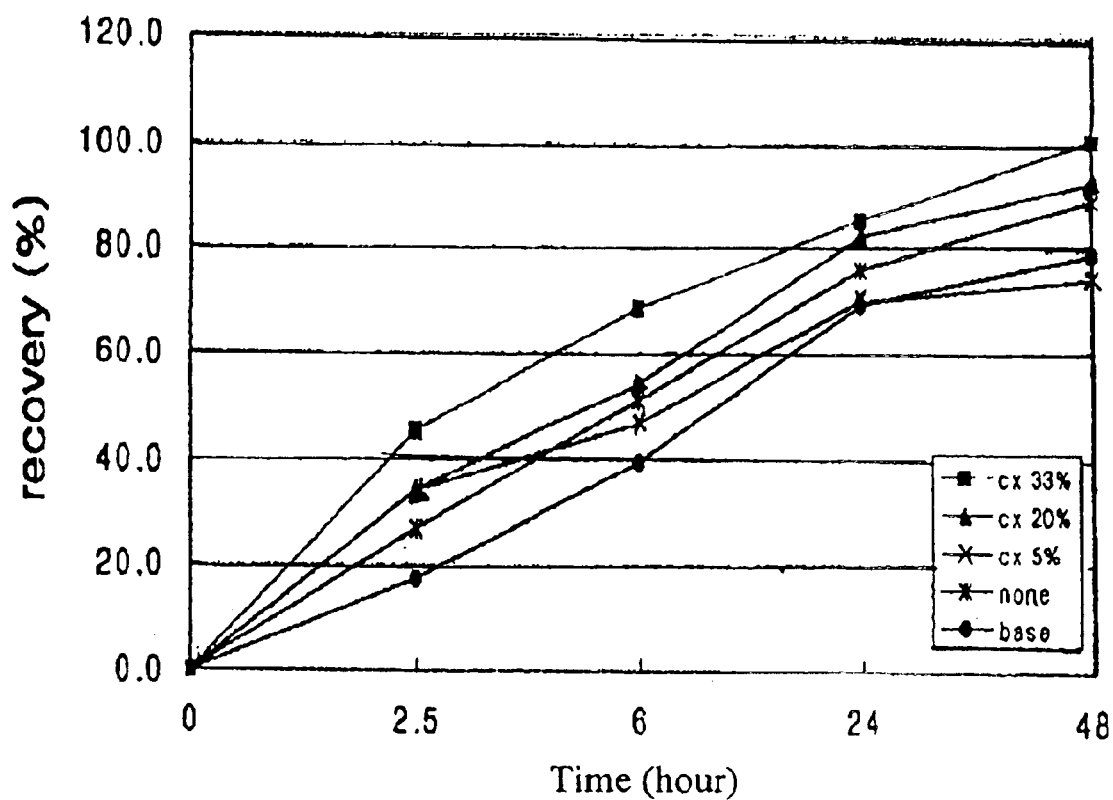
FIG. 1 is a line graph showing a recovery rate of a damaged skin barrier by a composition of the invention for comparison with the control. "cx 33%" refers to the use of "Composition 1" of Example 1. The term "base" refers to the use of the "Comparative Composition", and the term "None" refers to the negative control.

In some embodiments of the invention, a pharmaceutical composition is provided which can be employed as an essential therapeutic agent for dermal disease caused by damage of a skin barrier, such as atopic dermatitis. The composition can repair a damaged skin barrier to a normal condition so as to recover the skin's properties of moisture-retaining capacity and selective permeability, thereby maximizing inhibition or alleviation of skin irritation due to external irritation. Therefore, the present invention is directed to a therapeutic composition for the treatment of a broad spectrum of skin diseases, comprising a sphingolipid long-chain base in combination with a functional phospholipid such as lysophosphatidic acid.

One of advantages of a composition of the invention is that it exerts a similar efficacy to steroid hormone preparations and antibiotics which are mainly used for the treatment of atopic dermatitis. In some embodiments of the invention, another advantage is that since essential components of the composition, that is, ceramide, sphingolipid long-chain base and lysophosphatidic acid, are naturally present in the skin, its long-term use does not exhibit any side effects due to normal metabolism of such components.

Ceramide, a type of sphingolipid, is a primary component of skin lipids which is vital for retaining moisture. Ceramide has been employed as a functional ingredient of cosmetics. According to one research report, ceramide content in atopic skin, psoriasis lesions and skin afflicted with acne is lower than that of normal skin. Further, it was reported that the content of ceramide 3, among 6 ceramides in atopic skin, is reduced by more than 40% relative to normal skin, proving that the quantity of ceramide 3 in the skin is directly related to a variety of skin diseases.

A skin moisturizing effect of ceramide is driven by two fundamental underlying properties thereof. First, skin barriers take the form of keratinized dead cells stacked in a brick-like formation. The regions between the cells are filled with lipids being composed of mainly ceramides, cholesterol and fatty acids with an appropriate ratio (such as, for example 45%:25%:25%). This formation is is described as a bricks and mortar model, thereby forming a lipid lamellar barrier which prevents loss of moisture. Once a skin barrier is damaged, the skin cells synthesize new components that contribute to the skin barrier. At this time, ceramides are supplied for the last time. As a result, where the ceramide content in the skin is deficient, the damaged skin barrier is not quickly repaired, thereby failing to maintain moisture within the skin. The second property for skin moisturization by ceramides is that about a third of the moisture in the skin is bound to ceramides, that is, ceramides are present as a water-bound form. Thus, ceramides are a decisive factor responsible for maintaining moisture in the skin, among lipids composing the skin barrier.

Ceramides have been considered to be useful, so far, simply as a moisturizer, based on a limited consideration that a damaged skin barrier reflects only the decreased moisture retaining capability thereof. However, the skin barrier functions as a barrier against penetration of skin-irritating allergens or toxic substances, as well as maintaining skin's moisture balance. Accordingly, the damaged skin barrier results in a more severe condition leading to dysfunction of the barrier against allergens or toxic substances. Indeed, there is a report that patients afflicted with lamellar ichthyosis, whose skin barriers are severely damaged, experience acute toxic reactions to salicylic acid or lindane (JAMA 151: 372–374, 1953; Arch. Dermatol., 123: 1056–1058, 1987; which are incorporated by reference herein in their entireties).

The stratum corneum, responsible for moisture retention of the skin, contains 6 kinds of ceramides. These ceramides are divided into ceramides 1, 2, 3, 4, 5, and 6, according to the structures of their precursors, such as, for example, sphingosines or phytosphingosines. Ceramides found in the stratum corneum are pure ceramides, which have no sugar, phosphate, or choline groups, and are hydrophobic. Ceramides in the human skin have unique natural stereochemical structures. Actually, only ceramides with natural structures can repair the damaged stratum corneum to a normal state. Accordingly, since animal or plant ceramides exist as a sugar-bound form, such ceramides are not suitable for use to recover the damaged skin barrier. Also, since chemically synthesized ceramide analogs are not subjected to a natural metabolism in the skin layers and are accumulated therein, their long-term use can rather cause skin barriers to be damaged. Further, synthetic ceramide analogs lack the physiological activities of natural ceramides.

Among the 6 kinds of ceramides present in the skin, ceramide 3 in particular is closely related with transepidermal water loss (TEWL) (Acta. Derm. Venereol., 78: 27–30, 1998; which is incorporated by reference herein in its entirety). Patients with atopic dermatitis have a conspicuously low content of ceramides in skin lipids, even in the skin of non-lesion areas. This suggests that there is a need for a composition for application to the whole body or for a daily use, which strengthens skin barrier functions to prevent a possibility that non-lesions are likely to progress to lesions, in combination with a topical composition for the treatment or alleviation of lesions in patients with atopic dermatitis.

In the following, a description is given of effects of a therapeutic composition of the invention for the treatment of a broad spectrum of skin diseases.

Alleviation of Inflammation Such as Erythema and Improvement of Hypersensitive Skin Generally, anti-inflammatory agents inhibit protein kinase C (referred to hereinafter as PKC), and many PKC activity-inhibiting agents have been developed and employed as anti-inflammatory agents. In the biochemical pathway of inflammation induction, PKC activity increases due to exogenous stimuli, followed by an increase in phospholipase D (referred to hereinafter as PLD) activity, thereby proceeding to inflammation.

Sphingolipid long-chain base was found to significantly inhibit PKC and PLD activities. Further, sphingolipid long-chain bases have an excellent PKC inhibition effect in comparison to a skin irritation-relieving agent containing glycyrrhizins, which is now commonly employed as a skin irritation-relieving agent.

Meanwhile, adrenal cortical hormone preparations exhibit an effect of decreasing an expression level of marker molecules on the surface of Langerhans cells or reducing an antigen-presenting ability of the cells.

It is known in the art that UV radiation can be applied for the treatment of atopic dermatitis, regulating the density or antigen-presenting ability of Langerhans cells in the skin. The application of sphingolipid long-chain base including tetraacetyl phytosphingosine to the skin causes the cell density of Langerhans cells to decrease by 50 to 80%. From these results, it is expected that the composition of the invention would be effective to relieve symptoms such as pruritus and rash caused by hypersensitivity of the skin.

Therefore, a composition comprising sphingolipid long-chain base only, or a combination of 2 to 3 substances selected from the group of derivatives thereof, can exhibit the same functions as conventional steroid hormone agents or immunosuppressive agents, without a risk of side effects.

Wound Healing and Control of Resident Pathogens in the Skin

Patients with atopic dermatitis have been found to have about a 10 to 20 times higher cell count of the pyogenic bacteria *Staphylococcus sp.*, in lesion areas of the skin than in normal skin. Many patients suffering atopic dermatitis create wounds by scratching the skin due to itching, during their sleep. *Staphylococcus aureus* is the bacteria infecting the lesions at this time, and is a factor causing inflammation in atopic dermatitis. In addition, the bacteria secrete enzymes which degrade ceramides in the stratum corneum, causing a deficiency in ceramides (Int'l. J Dermatology, 29: 579–582; 1990; which is incorporated by reference herein in its entirety).

It has long been known that antibacterial substances exist in the stratum corneum, constructing a primary defense system against invading bacteria. Recent findings have shown that antibacterial substances are precursors of ceramides such as sphingosine and phytosphingosine, as reported by scientists at the College of Medicine at the Univ. of California. Thus, it is expected that by using such natural substances, generation of resistant bacteria due to a current overuse of antibiotics can be prevented, while chronic skin diseases can be treated. With regard to such antibiotic-resistant bacteria, a 10 year long clinical pathological investigation was performed at Leeds University of U.K. According to the research, antibiotic resistant bacteria were detected in more than 60% of the patients who had previously applied antibiotics for the treatment of skin diseases including acne, for a long-term period.

Steroid hormone preparations, retinoid preparations, immunosuppressive agents, and antibiotics have been commonly used for the treatment of eczema, atopic dermatitis, psoriasis, pruritus, ichthyosis, acne, inflammation, erythema, and bacterial infections accompanying with dysfunctions of the skin barrier. In some embodiments of the invention, a composition effective to the treatment of a broad range of skin diseases, without the use of such agents mentioned above, is provided.

As an active ingredient of the composition according to the invention, sphingolipid long-chain base can be used instead of steroid hormone preparations or retinoid preparations having an anti-inflammatory effect, immunosuppressive agents having an effect of alleviating skin irritation, and antibiotics, which can greatly reduce the amounts and frequencies of required applications. The harshly scratched wounds due to severe pruritus, and fissures in the skin should be healed.

In some embodiments, the sphingolipid long chain base can be present at a level of about 0.001%, 0.01%, 0.05%, to about 2%, 4%, 6%, 8%, or 10% by weight. Particularly useful embodiments include sphingolipid long chain base at a level between about 0.1%, 0.3%, or 0.5%, and about 0.6%, 0.7%, or 1.0% by weight.

As another ingredient of the composition, lysophosphatidic acid has an effect of regenerating the damaged skin tissues and new blood vessels. Lysophosphatidic acid exerts a synergistic effect in repairing the damaged skin tissues and scars when applied in combination with sphingolipid long-chain base at respectively adequate amounts.

In some embodiments, the lysophosphatidic acid can be present at a level of between about 0.0001%, 0.0005%, 0.001%, or 0.0025% to about 0.6%, 1.0%, 3%, 5%, 7%, or 10% by weight. Particularly useful embodiments include lysophosphatidic acid at a level of between about 0.05%, 0.07%, 0.1%, to about 0.15%, 0.2%, 0.4% by weight.

Lysophosphatidic acid, along with lysophosphatidyl choline, is present in many cell membranes of organisms, and is one of important phospholipids involved in transmembrane signaling. In the transmembrane signaling pathway, lysophosphatidic acid increases $Ca^{++}$ concentration in the cytoplasm, and is involved in activation of a mitogen-activated protein kinase. It is known that lysophosphatidic acid serves as a mediator involved in inflammation and plays roles in thrombosis. Lysophosphatidic acid is also a factor involved in growth and contraction of smooth muscles and fibroblasts. Further, it is involved in induction of vascular cell adhesion molecules, together with sphingosine-1-phosphate. It is secreted from activated platelets. It can be expected that lysophosphatidic acid is involved in asthma, an inflammatory respiratory disease. Moreover, since it is involved in expression induction of vascular cell adhesion molecules, accordingly, it is considered that it is closely linked to quick wound healing and formation of new blood vessels.

Meanwhile, the damaged skin tissues should be regenerated in terms of the dermis, epidermis, and the stratum corneum. For the recovery of these skin barriers, it is necessary to supply ceramide, a primary constituent in the stratum corneum lipids. According to U.S. Pat. No. 5,578,641, when sphingolipid long-chain base is topically applied to the skin, synthesis of ceramide is increased by more than 50%. However, biosynthesis of ceramide is normally occurs later than that of other skin lipids. In some embodiments of the invention, ceramide is compounded with cholesterol and fatty acid (which are the main lipid constituents of the skin barrier) at an appropriate ratio, by employing other bases for formulation, thereby maximizing the pharmaceutical efficacy of sphingolipid ling-chain base and lysophosphatidic acid.

The sphingolipid long-chain base described in Example 1 was prepared according to a method disclosed in U.S. Pat. No. 5,958,742. However, the sphingolipid long-chain base useful for the invention may be prepared by any suitable method, such as, for example, isolation and purification from natural sources, synthetic preparation, or other methods.

Lysophosphatidic acid useful for the invention may be prepared by any suitable method, such as, for example, isolation and purification from natural sources, synthetic preparation, or other methods. Lysophosphatidic acid used herein was obtained by fractionation and purification of lecithin isolated from egg yolk or beans. Alternatively, as for lysophosphatidic acid, lyso-stearoyl phosphatidic acid (18:0), lyso-oleoyl phosphatidic acid (18:1), or lyso-palmitoyl phosphatidic acid (16:0) was used. Sphingolipid long-chain bases such as phytosphingosine, N-acetylphytosphingosine and tetraacetyl phytosphingosine, exhibit several common effects, such as the inhibition of protein kinase C and phospholipase D, antibacterial activity, and promotion of ceramide synthesis in the skin cells. It was also found that sphingolipid long-chain bases listed above show a significant difference in terms of their physical properties, despite their similar effects. Moreover, formulations for topical application containing tetraacetyl phytosphingosine exhibited excellent functionalities in terms of compatibility with other ingredients, solubility, stability, and transdermal absorption. Formulations Containing Sphingolipid Long Chain Base Combined with Lysophosphatidic Acid In preferred embodiments of the invention, the composition is formulated into a cream that can be topically applied to the skin. An example of such a formulation is shown in Example 1. The formulations of the invention can also be prepared into any other suitable forms. Examples of such formulations include but are not limited to a lotion, an ointment, a skin toner, an essence, a body wash, a spray, a shampoo, and the like.

In other embodiments of the invention, the compositions of the invention may be formulated into a shampoo to treat diseases of the scalp. Any suitable shampoo composition can be used as the base shampoo material, to which the desired sphingolipid long-chain base and desired lysophosphatidic acid are added. An example of a shampoo composition that can be used to practice the invention is shown in Example 8. In addition to the presence of sphingolipid long-chain base and lysophosphatidic acid, the shampoo compositions may contain other ingredients typically employed in these compositions. Examples of such additional ingredients include but are not limited to detergents, complexing agents, dyestuffs, preservatives, pH-regulators, viscosity regulators, fragrances, thickeners, and the like. Additional components for shampoo formulations are described, for example, in U.S. Pat. No. 5,439,673, the disclosure of which is incorporated by reference herein in its entirety.

In some embodiments of the invention, the compositions of the invention may be formulated into a body wash for the treatment of the skin. Though any suitable body wash recipe may be used as a base composition for a sphingolipid long-chain base and lysophosphatidic acid-containing body wash, an example of a body wash composition is provided in Example 9. In addition to the presence of sphingolipid long-chain base and lysophosphatidic acid, a body wash composition may contain other ingredients typically employed in these compositions. Examples of such additional ingredients include but are not limited to anionic surfactants, nonionic surfactants, amphoteric surfactants, a polymeric cationic conditioning compound, a quaternized phosphate ester, dyes, preservatives, emulsifiers, conditioning agents, inorganic salts, humectants, pH-regulators, solubilizers, thickeners, viscosity regulators, fragrances, acids, alkalis, buffers, oils, and the like. Suitable base compositions for a body wash can be found, for example, in U.S. Pat. No. 5,683,683, the disclosure of which is incorporated by reference herein in its entirety.

In some embodiments of the invention, the compositions of the invention may be formulated into an ointment. Examples of ointment base formulations can be found, for example, in U.S. Pat. No. 5,336,692, the disclosure of which is incorporated by reference herein in its entirety. An example of an ointment composition of the invention is shown in Example 10. In addition to the presence of sphingolipid long-chain base and lysophosphatidic acid, an ointment of the invention may contain, for example, high molecular weight petrolatum fractions combined with a solvent material for the petrolatum fractions. The high molecular weight petroleum fraction material is typically chosen so that it is physiologically tolerable with little or no white oil remains. Examples of additional compounds that are typically used in ointment preparations include but are not limited to aromatic alcohols, aliphatic alcohols, silanyl alcohols, aldehydes, esters, ketones, benzyl alcohol, benzaldehyde, phenylethyl alcohol, benzyl glycolate, benzophenone, silanyl aldehydes, silanyl esters, silanyl ketones, and the like.

The above disclosure generally describes the present invention. A more complete understanding can be obtained by reference to the following specific examples which are provided herein for purposes of illustration only and are not intended to limit the scope of the invention.

EXAMPLE 1

Acute Repair of Skin Barrier

A therapeutic composition for atopic dermatitis was formulated to a cream by adding ceramide, sphingolipid long-chain base and lysophosphatidic acid to conventional basic cream ingredients, according to the formula shown in "Composition 1" in Table 1, below.

TABLE 1

Formulation of cream (unit: % by weight)

| | Composition 1 (The present invention) | Comparative Composition |
|---|---|---|
| ceramide | 1.17 | 0 |
| sphingolipid long-chain base | 0.495 | 0 |
| cholesterol | 0.825 | 0 |
| free fatty acid | 0.99 | 0 |
| lysophosphatidic acid | 0.1 | 0 |
| glycerin | 4 | 4 |
| 1,3-butylene glycol | 2 | 2 |
| Carbopol 940 | 0.2 | 0.2 |
| triethanolamine (TEA) | 0.18 | 0.18 |
| Germall 115 | 0.2 | 0.2 |
| phytosqualane | 15 | 15 |
| DC-345 | 5 | 5 |
| miscellanies | 31.92 | 35.5 |
| distilled water | 37.92 | 37.92 |

An acute repair of skin barrier test was performed to examine the recovering effect of moisture barrier function in the skin by Composition 1.

Hairless mice of ages 8 to 12 weeks were used for the skin repair test. Transepidermal water loss (TEWL) was measured in two areas on the back of each mouse (TEWL value of the normal skin lies approximately $10\pm2$ g/cm$^2$/hr). Subsequently, the same areas of the back were stripped 5 to 10 times with Scotch tape. The tape-stripping procedure was repeated until the TEWL values reached around 40 to 50 g/cm$^2$/hr. For application of a cream of the invention thus formulated, One damaged area of the back was topically treated with either Composition 1 or a basic cream ("Comparative Composition") t at intervals of 12 hrs (immediately, 12 hrs, and 36 hrs after injury). The other area of the damaged skin was not treated, serving as a control. Measurements of water loss were performed, along with a lapse of time (immediately, at 2 hr, 6 hr, 24 hr, and 48 hr after injury). Skin recovery was calculated by the normalization of transepidermal water loss.

TABLE 2

Skin recovery (%)

| Time after damage (hrs) | Composition 1 | Control | Comparative Composition |
|---|---|---|---|
| 0 | 0.0 | 0.0 | 0.0 |
| 2 | 45.1 | 27.1 | 17.5 |
| 6 | 68.5 | 51.1 | 39.2 |
| 24 | 85.6 | 75.9 | 69.4 |
| 48 | 100 | 89.6 | 79.1 |

FIG. 1 is a graph showing a recovery rate of the skin barrier by a composition according to the invention, wherein "cx 33%" represents a preferred embodiment of the composition of the invention (Composition 1); and "base" represents a basic cream (Comparative Composition). As shown in Table 2 and FIG. 1, the composition according to the invention accelerated recovery of the skin barrier, compared to the control (no treatment) and the Comparative Composition. It was found that 100% recovery was accomplished at 48 hrs. That is, Composition 1, comprising sphingolipid long-chain base and lysophosphatidic acid, promoted full recovery of the skin moisture barrier in 48 hrs.

Figure 2A:
FIG. 2a is a photograph showing skin tissue treated with a composition of the invention after acute disruption of the skin.
Figure 2B:
FIG. 2b is a photograph showing skin tissue without treatment after acute disruption of the skin (Control).

In addition, as shown in FIGS. 2a and 2b, the examination of skin tissues by means of microscopy revealed that the composition of the invention improves regeneration of the stratum corneum, compared to the untreated control.

EXAMPLE 2

Clinical Evaluation in Patients with Atopic Dermatitis

To evaluate the composition according to the present invention for the treatment of atopic dermatitis, patients with atopic dermatitis were involved in a clinical test.

Skin conditions of the patients were examined in both lesion areas and non-lesion areas. Parameters such as transepidermal water loss, skin hydration, pH and cell density of *Staphylococcus sp.* were measured. After applying the composition to the lesion areas twice per day for 2 weeks, the extent of improvement of the skin was determined by comparison with control values.

Also, alleviation effects of the composition of the invention on atopic dermatitis were evaluated by a comprehensive analysis in terms of accompanying wound conditions such as itch, erythema and inflammation.

TABLE 3

Changes of skin condition

| | | Initial skin conditions | | | | Skin conditions after application for 2 weeks | | | |
|---|---|---|---|---|---|---|---|---|---|
| Subject | Parameter | TEWL | Hydration | pH | No. m/o | TEWL | Hydration | PH | No. m/o |
| Case 1 | lesion | 64 | 26 | 7.2 | 154 | 16.6 | 46 | 5.7 | 39 |
| | non-lesion | 14 | 53 | 5.7 | 30 | 13 | 55 | 5.5 | 15 |
| Case 2 | lesion | 36.8 | 31 | 4.9 | 148 | 20.4 | 41 | 5.3 | 48 |
| | non-lesion | 16.7 | 50 | 5.4 | 12 | 12.7 | 51 | 5.4 | 19 |
| Case 3 | lesion | 46.2 | 23 | 5.6 | 6400 | 23.4 | 39 | 5.2 | 327 |
| | non-lesion | 12.8 | 46 | 5.8 | 12 | 17.7 | 51 | 5.6 | 33 |
| Case 4 | lesion | 46.3 | 25 | 5.8 | 89 | 19.8 | 38 | 5.6 | 25 |
| | non-lesion | 17.9 | 39 | 6.2 | 3 | 16.9 | 46 | 5.5 | 5 |

TABLE 3-continued

Changes of skin condition

| Subject | Parameter | Initial skin conditions | | | | Skin conditions after application for 2 weeks | | | |
| --- | --- | --- | --- | --- | --- | --- | --- | --- | --- |
| | | TEWL | Hydration | pH | No. m/o | TEWL | Hydration | PH | No. m/o |
| Case 5 | lesion | 48.5 | 45 | 4.7 | 65 | 20.5 | 47 | 5.2 | 33 |
| | non-lesion | 16 | 54 | 5.2 | 6 | 15.6 | 54 | 5.2 | 8 |

As can be seen in Table 3, there are large differences between lesion areas and non-lesion areas in patients with atopic dermatitis, among all parameters tested. As for the TEWL, lesion areas have very high values in all patients, compared to the normal skin with a TEWL value of around 10±2 g/cm$^2$/hr. Compared with a normal value of hydration (50 to 60), the skin lesion areas show a very low hydration, indicating water loss in lesion areas. This shows that the skin's stratum corneum barrier is severely damaged, resulting in excessive loss of moisture. Also, the pH of the lesion areas is measurably different from around 5.5, which is the pH value of healthy skin. As for the distribution of microorganisms, although their densities can vary according to the patients, the lesion areas commonly showed a high density of microorganisms, compared to the non-lesion areas of the patients. It can be inferred that secondary infection readily occurs in the lesion areas, as the patients scratch to relieve itching.

The damaged skin could be recovered, however, by applying the composition of the invention for 2 weeks. As a result, TEWL was greatly decreased, and hydration of the skin was greatly increased so as to significantly rejuvenate the dry skin. In addition, the application of the composition caused a decrease in the dry feeling of the skin, so that itching was relieved, leading to the cessation of scratching, whereby a secondary infection was prevented. Accordingly, the regional distribution of microorganisms in the lesion areas was largely decreased, in comparison to its initial value.

This decrease in microorganisms and decrease in scratching led to eventual repair of erythema and repair of wounded skin (Table 4). Moreover, it was found that the itching reduction upon application of the composition led to a remarkable improvement in self-consciousness of the patients, in comparison to pre-application levels.

TABLE 4

Changes in symptoms of skin disorders

| | Pre-application | | | Post-application for 2 weeks | | |
| --- | --- | --- | --- | --- | --- | --- |
| | itching | erythema | wound | itching | erythema | wound |
| Case 1 | +++++ | ++++ | +++++ | + | ++ | ++ |
| Case 2 | +++++ | +++ | ++ | ++ | + | + |
| Case 3 | +++++ | +++++ | +++++ | + | ++ | + |
| Case 4 | +++++ | +++ | +++ | + | + | + |
| Case 5 | +++++ | +++++ | +++++ | + | + | + |

Note:
The evaluation is as follows:
+: not severe,
+++++: very severe.

EXAMPLE 3

Wound Repair in Rabbits

As an experimental animal model, female New Zealand White rabbits (2 kg in body weight) were employed to evaluate the efficacy of phytosphingosine and derivatives thereof on wound healing.

The rabbits were anesthetized with an intramuscular injection of ketamine (3 to 4 mg/kg). After removing hairs and a horny layer (stratum corneum) inside the both ears, 4 full-thickness circular wounds were created in each ear using a 6 mm-punch biopsy. As a control, PBS solution containing 0.1% BSA was applied to the wound regions at an amount of 10 $\mu$l every second day. For test groups, a composition comprising lysophosphatidic acid only, a composition comprising sphingolipid long-chain base only, and a composition comprising a combination thereof were applied each at varying concentrations (5 $\mu$M, 10 $\mu$M and 50 $\mu$M) at a volume of 10 $\mu$l every second day. The wounds applied with those agents were sealed with Cathreep (Nichiban Co., Japan). On 4$^{th}$ and 8$^{th}$ day after application, the rabbits were sacrificed, and the wound areas were histologically examined.

Figure 3:
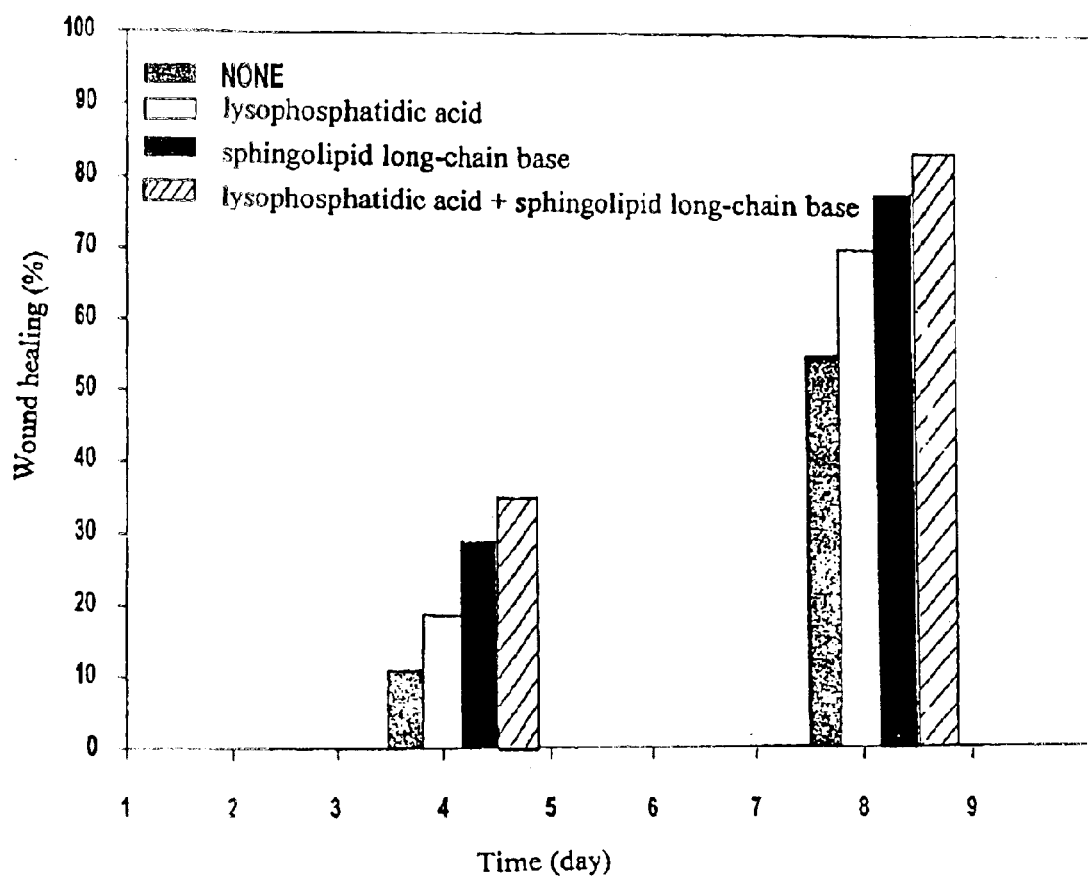
FIG. 3 is a bar graph showing the effects of sphingolipid long-chain base, lysophosphatidic acid, or both, on wound repair.
Figure 4A:
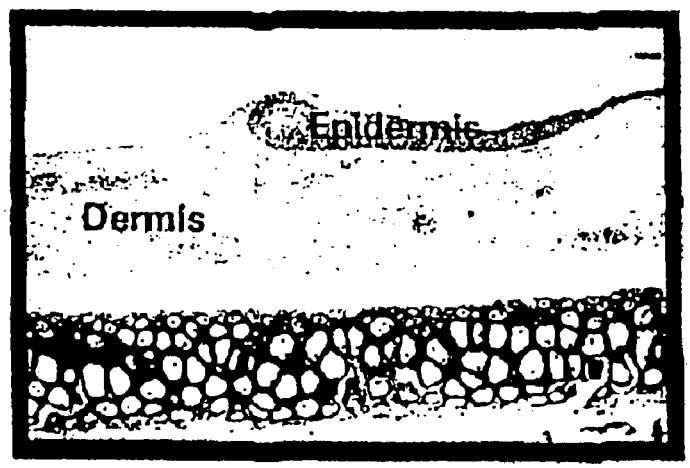
FIGS. 4a and 4b are photographs showing regeneration of the epidermis and dermis through formation of the stratum granulosum (granular layer) by treatment of a composition of the invention.
Figure 4B:
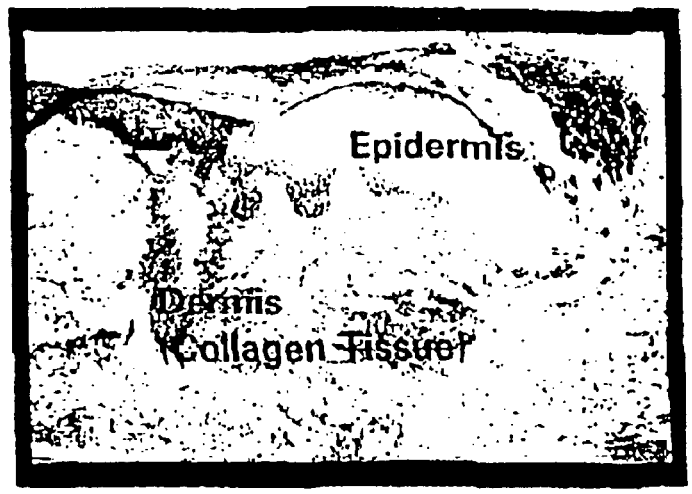

FIG. 3 is a graph showing the effects on wound repair by the composition comprising sphingolipid long-chain base and lysophosphatidic acid. The extents of wound repair in the skin were compared with an untreated control group. It can be seen that phytosphingosine and derivatives thereof, or/and lysophosphatidic acid treatments highly accelerate the rates of wound healing (%), compared to the untreated control group (FIG. 3). Moreover, as revealed in histological examination, it was observed that where the treatments were applied, regeneration of the epidermis and dermis through formation of the stratum granulosum (granular layer) are very rapidly promoted (FIGS. 4a and 4b). New blood vessel formation was also observed.

EXAMPLE 4

Effect on Langerhans Cells

Langerhans cells play a role in mediating immune response of the skin. Treatment of skin disorders related to a hypersensitive immune response can be accomplished by regulating either the number or the antigen-presenting ability of Langerhans cells. To examine the efficacy of sphingolipid long-chain base on the regulation of the number of Langerhans cells, a test was performed as follows. Each skin explant was applied with a 1% test sample containing sphingolipid. Histological analysis revealed a 26 to 65% decrease in the number of Langerhans cells when the test sample contained sphingolipid, compared to a negative control. Specifically, the efficacy of phytosphingosine on reducing the number of Langerhans cells was greater than that of tetraacetyl phytosphingosine.

EXAMPLE 5

Anti-microbial Test

To assess antimicrobial activity of tetraacetyl phytosphingosine versus harmful microorganisms in the skin, diverse bacteria and fungi were employed. Included were *Propionibacterium acnes, Staphylococcus aureus, Bacillus subtilis, Micrococcus sp., Aspergillus niger*, and *Pityrosporum ovale*, which is a bacterium causing dandruff.

A culture medium for *Propionibacterium acnes* was prepared as follows. First, with respect to 1 L distilled water, 25 g brain heart infusion agar, 5 g yeast extract, 4 g Casitone, 1 g L-Cysteine HCl, 5 g glucose, 1 g soluble starch, 15 g monopotassium phosphate, 1 g ammonium sulfate, 0.2 g magnesium sulfate, and 0.02 g calcium chloride were homogeneously dissolved and autoclaved. The bacterial culture was grown at 37° C. for about 3 to 5 days under anaerobic conditions using a BBL GasPak anaerobic system. The bacterial count was measured and the antibacterial ability was determined.

As respective media for other microorganisms, *Staphylococcus* medium 110 (Difco, USA) was used for *Staphylococcus aureus*, Nutrient agar for *Bacillus subtilis* and *Micrococcus sp.*, and Potato Dextrose agar (Difco, USA) for *Aspergillus niger*. For *Pityrosporum ovale*, a medium containing 0.1% peptone, 0.5% glucose, 0.01% yeast extract, 0.4% Oxbile, 0.05% glyceryl monostearate, 0.1% whole milk powder, and 0.1% glycerol, by weight relative to the total medium weight, was prepared.

Samples of tetraacetyl phytosphingosine employed in the invention were prepared by dissolving in ethanol. To evaluate the antimicrobial activity, samples of tetraacetyl phytosphingosine were prepared and used at final concentrations of 1 µg/ml, 10 µg/ml, 100 µg/ml, and 1000 µg/ml. The test microorganisms were cultured in the respective liquid media, and the cultures were 10-fold serially diluted. At this time, the diluent was 0.85% NaCl. The dilution ratios were determined to adjust the microorganisms to form about $10^3$–$10^4$ colonies per an agar plate if they are grown without any tetraacetyl phytosphingosine samples.

1 ml each of the samples containing tetraacetyl phytosphingosine at the desired concentration, and 9 ml of each of the adequately diluted solutions containing microorganisms were mixed and blended well. The mixed solutions were allowed to stand at 37° for 30 min to 1 hr, with occasional blending. The solutions were smeared at 100 µl each on the respective agar plates. As a control, the solvent (ethanol) used in dissolving the samples was applied. The plates were incubated under respective appropriate culture conditions, and microbial colonies were counted.

Figure 5:
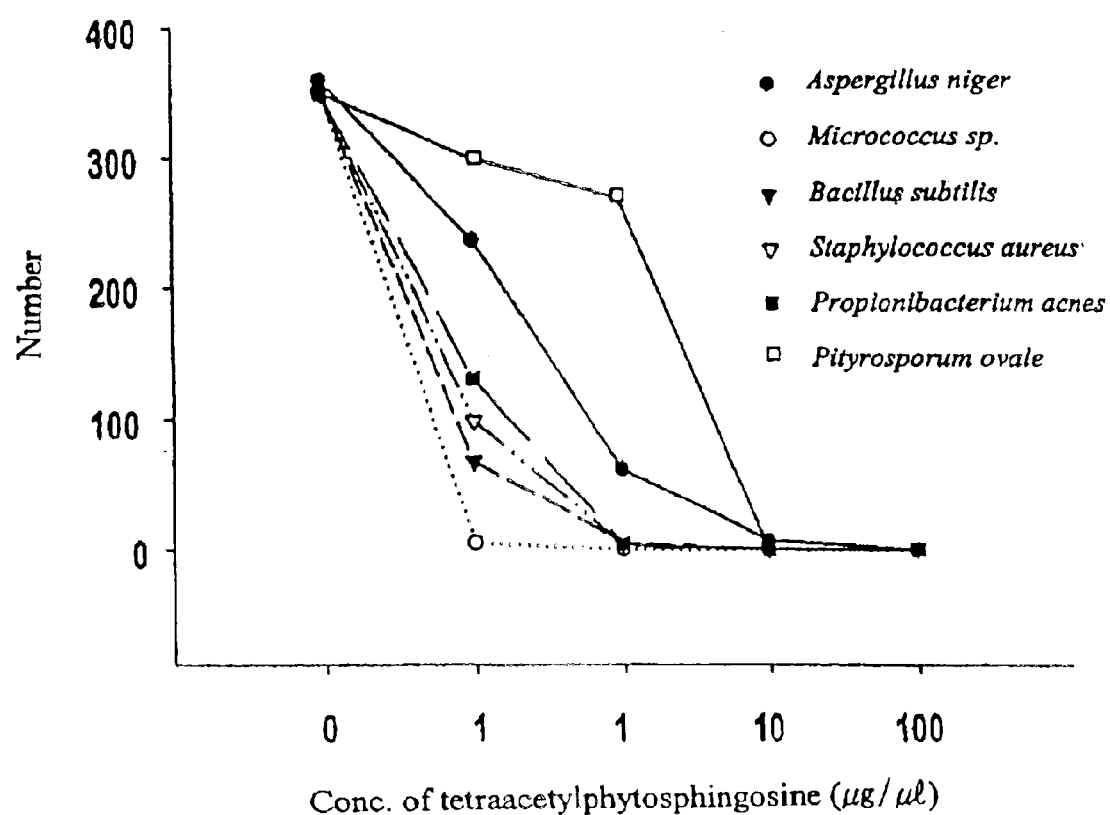
FIG. 5 is a line graph showing the antimicrobial activity of tetraacetyl phytosphingosine versus microorganisms.

The results are shown in FIG. 5, which is a graph showing an antimicrobial activity of tetraacetyl phytosphingosine on respective microorganisms employed herein.

EXAMPLE 6

Effect on Anti-inflammation

An anti-inflammation effect of the cream composition according to the invention was evaluated by assessing inhibition of protein kinase C (PKC) in mouse epidermal cell line (Pam212). The cultured epidermal cells at $2 \times 10^7$ cells/ml were treated with phytosphingosine or derivatives thereof at final concentrations of 100 µM, and 400 µM. After washing with PBS, the cells were disrupted using a homogenizer and centrifuged. The supernatant was passed through a DE52 column to obtain a fraction containing PKC. To measure the amount of activated PKC in the fractions, 5 µl each of a PKC coactivation 5× buffer, PKC activation 5× buffer, PKC biotinylated peptide substrate and $^{32}$P-ATP mixture were added to a tube. For a negative control, 5 µl each of a PKC coactivation 5× buffer, Control 5× buffer, PKC biotinylated peptide substrate and $^{32}$P-ATP mixture were measured. To the tubes were added 5 µl of respective PKC fractions. The reaction was performed at 30° C. for 5 min. After terminating the reaction by adding a 12.5 µl stop solution, a 10 µl aliquot was dropped on a SAM$^{2\text{TM}}$ membrane. The membrane was washed 1× with 2M NaCl for 30 sec, 3× with 2M NaCl for 2 min, 4× with a solution of 1% $H_3PO_4$ and 2M NaCl for 2 min, and 2× with distilled water for 30 sec, followed by drying. Radioactivity was measured to examine a PKC inhibition effect.

Figure 6:
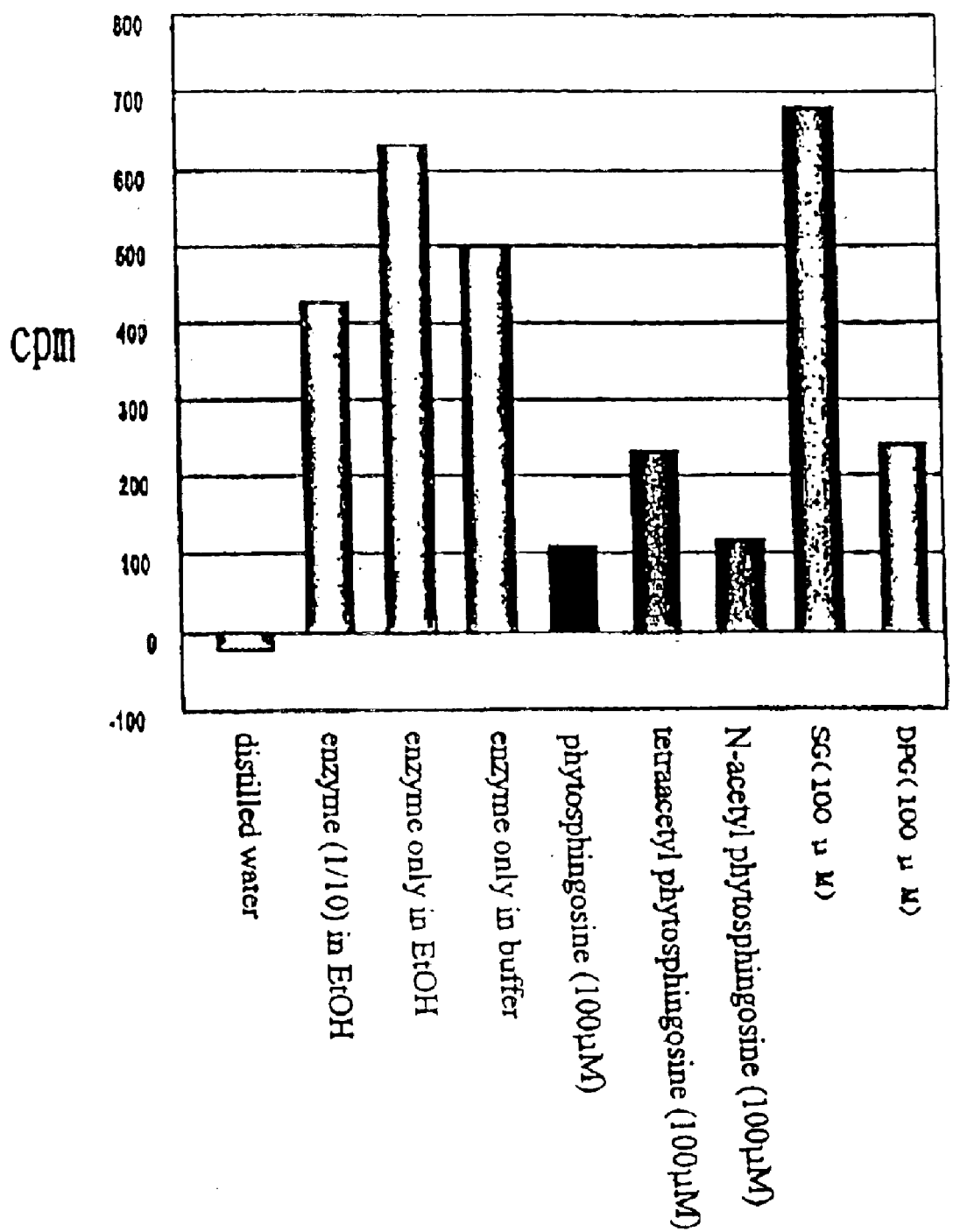
FIG. 6 is a bar graph showing the inhibitory effects of sphingolipid long-chain base on protein kinase C activity.

The results are shown in FIG. 6. Phytosphingosine, tetraacetyl phytosphingosine, and N-acetyl phytosphingosine showed excellent PKC inhibition effects, even at low concentrations. In FIG. 6, SG and DPG refer to licorice extracts. As shown in FIG. 6, it was found that the treatment of sphingolipid long-chain base inhibits the activity of PKC. Meanwhile, it is known that in a biochemical pathway involved in inflammation induction, PKC activation is increased by exogenous stimulation, and then phospholipase D (abbreviated by PLD) activation is increased, proceeding to inflammation. The above results demonstrate that since treatment of the composition according to the invention inhibits PKC activation, the resulting inflammation can be inhibited. Further, it can be seen that sphingosine long-chain bases exert a greater PKC inhibition effect than licorice extracts, a stimuli-relieving agent containing glycyrrhizins, which have been mainly employed for the manufacture of cosmetics.

EXAMPLE 7

Tracing a Metabolic Pathway of Tetraacetyl Phytosphingosine in Skin Cells

It is known that topical application of tetraacetyl phytosphingosine (TAPS) and phytosphingosine (PS) increase synthesis of glucosyl ceramide in skin cells by more than by 50%. However, it is not yet reported which pathway provides such an activity of TAPS after being penetrated into the cells. The inventors performed experiments to examine effects of diverse phytosphingosine derivatives including TAPS on human skin fibroblasts, and examine a pathway for metabolism thereof.

Human skin fibroblasts were employed as the cell line for the study. Phytosphingosine, tetraacetyl phytosphingosine, and acetyl phytosphingosine were respectively dissolved in a mixture of ethanol/dodecane, preparing stock solutions at certain concentrations. When the fibroblasts became confluent in 7 cm diameter culture dishes, 20 µM of the respective test samples was added and cultured in a $CO_2$ incubator for 48 hrs. Cells were harvested and treated according to a common extraction method for sphingolipids. Hydrolysis was performed under basic conditions at 37° C. overnight. The samples were passed through a reverse phase column to remove salts. The desalted lipid extracts were subjected to a TLC analysis on Silica gel 60 G plates (Merck, Germany), using chloroform/methanol/concentrated acetic acid (190/9/1) to elute neutral lipids.

It was found that sphingolipid long-chain bases including TAPS at an amount of 20 µM (total medium volume in a dish: 6 ml; absolute amount treated: 83.3 nmol) do not affect the growth and morphology of fibroblasts (data not shown). This indicates that phytosphingosine and derivatives thereof including TAPS exhibit no toxicity on fibroblasts, which compose the dermis. The results show that TAPS is converted to C2-phytoceramide within the cells, where it accumulates. It can be inferred that acetyl groups added to three —OH groups of TAPS are lost, thereby TAPS being converted to C2-phytoceramide. In general, since the metabolism rate of C2-phytoceramide is slower than natural ceramides, about 60 to 70% of C2-phytoceramide remains within the cells at 24 hrs after entering the cell (Hannun et al., J Biol. Chem, 1993).

These results prove that TAPS converts to a metabolic intermediate of natural sphingolipids in the skin cells so as to exert its physiological functions, although TAPS has a chemical structure different from that of sphingolipids present in human skin. In addition, TAPS has lower cytotoxicity than other sphingolipid long-chain bases. The reason for this is that TAPS is converted to an active form thereof in the cell, with a lapse of time, not that its physiological activity is weak.

EXAMPLE 8

Shampoo composition

| Ingredient | (% by weight) |
|---|---|
| acetylphytosphingosine | 5% |
| Lyso-stearoyl phosphatidic acid (16:1) | 1.0% |
| Sodium lauryl sulphate | 16.0% |
| Lauryl betaine | 2.0% |
| PFPE (Fomblin HC/04) | 0.0003% |
| Dimethicone (60,000 cS) | 0.25% |
| Polymer JR 400 | 0.3% |
| Ethylene glycol distearate | 1.5% |
| Formalin | 0.1% |
| Water | to 100% |

The above ingredients are prepared and packaged for consumer use. To treat scalp diseases, the shampoo is used preferably once a day, with one or two washings followed by a rinse with cool water.

EXAMPLE 9

Body wash composition

| Ingredient | (% by weight) |
|---|---|
| Phytosphingosine | 0.02% |
| Natural lyso-phosphatidic acid derived from egg yolk | 0.05% |
| Sodium Lauryl Ether Sulfate | 11.0% |
| Cocamide MEA | 8.0% |
| Preservative | 0.4% |
| Guar Hydroxypropyltrimonium chloride | 0.25% |
| Tetrasodium Ethylenediamine Tetraacetic Acid | 0.1% |
| Citric Acid | 0.2% |
| Palmitic Acid | 2.5% |
| Stearamidopropyl Phosphatidyl PG-Diamonium Chloride | 0.5% |
| Cocamidopropyl Hydroxysultaine | 2.0% |
| Titanium Dioxide | 0.15% |
| Water | to 100% |

The above composition is prepared and packaged under sterile conditions. To treat skin conditions, the composition is applied to the skin as for a typical body wash composition, on a daily or twice-a-day basis. The composition may be left on the skin for a few minutes, if desired. The skin is then rinsed thoroughly and towel dried.

EXAMPLE 10

Ointment composition

| Ingredient | % (by weight) |
|---|---|
| Hexanoylphytosphingosine | 3% |
| Lyso-palmitoyl phosphatidic acid (16:1) | 0.2% |
| Special Petrolatum Fraction (USP) | 5% |
| Octanol | 0.4% |
| Phenylethyl alcohol | 1.2% |
| Cyclomethicone | 10% |
| Dimethicone copolyol | 11% |
| Sorbitan laurate | 1.2% |
| Water | 68.0% |

The lipid and hydrophilic components are separately warmed and then mechanically mixed under shear. The ointment is then cooled to room temperature while stirring. The ointment is applied to the skin as needed to decrease the symptoms of atopic dermatitis or other skin diseases. Preferably, the ointment is applied several times a day, or as needed.

As apparent from the above description, the present invention provides a therapeutic composition for a broad spectrum of skin diseases, comprising sphingolipid long-chain base which include phytosphingosine and its derivatives and serve as one constituent for lipids of the skin, and lysophosphatidic acid which are phospholipids with various beneficial functionalities. Such a composition plays a role in repairing skin moisture barriers to maintain a normal state, and is capable of alleviating or relieving skin inflammation, itch, and dry skin, and bacterial infection, which are characteristics of atopic dermatitis.

It will be appreciated that no matter how detailed the foregoing appears in text, the invention can be practiced in many ways. It should further be noted that the use of particular terminology when describing certain features or aspects of the present invention should not be taken to imply that the broadest reasonable meaning of such terminology is not intended, or that the terminology is being re-defined herein to be restricted to including any specific characteristics of the features or aspects of the invention with which that terminology is associated. Accordingly, although the preferred embodiments of the present invention have been disclosed for illustrative purposes, those skilled in the art will appreciate that various modifications, additions and substitutions are possible, without departing from the scope and spirit of the invention as disclosed in the accompanying claims. All publications and patents cited in this disclosure are hereby incorporated by reference in their entireties.

What is claimed is:

1. A therapeutic composition for topical application, consisting essentially of:

a sphingolipid long-chain base present at from about 0.01 to 5.0% and lysophosphatidic acid present at from about 0.001 to 1.0%, wherein the sphingolipid long-chain base is one or more selected from the group consisting of phytosphingosine, acetylphtosphingosine, tetraacetyl phytosphingosine, hexanoylphytosphingosine and acetylphytosphingosine phosphate.

2. A therapeutic composition for topical application, consisting essentially of:

30 to 90% by weight of a substrate or a carrier for skin application;

0.01 to 5.0% by weight sphingolipid long-chain base;

0.001 to 1.0% by weight lysophosphatidic acid;

and 1.0 to 40% by weight of organic or inorganic additives, wherein the sphingolipid long-chain base is one or more selected from the group consisting of phytosphingosine, acetylphytosphingosine, tetraacetyl phytosphingosine, hexanoylphytosphingosine and acetylphytosphingosine phosphate.

3. The therapeutic composition according to claim 2, wherein the organic additives contain ceramide, cholesterol and fatty acid.

4. The therapeutic composition according to claim 3, wherein the organic additives contain a weight ratio of ceramide: cholesterol: fatty acid of from about 40 to 60%: from about 20 to 30%: from about 20 to 30%.

5. The therapeutic composition according to claim 2, wherein the ceramide comprises one or more selected from the group consisting of: ceramide 3 ceramide 6, and a mixture thereof, and wherein the ceramide has the same stereochemical composition as the ceramide in human skin lipids.

6. The therapeutic composition according to claim 1, wherein the lysophosphatidic acid is one or more selected from the group consisting of lyso-stearoyl phosphatidic acid (18:0), lyso-oleoyl phosphatidic acid (18:1), lyso-palmitoyl phosphatidic acid (16:0) and natural lyso-phosphatidic acid derived from egg yolk or beans.

7. The therapeutic composition according to claim 1, wherein the composition is formulated into a form selected from the group consisting of: a cream, a lotion, an ointment, a skin toner, an essence, a body wash, and a shampoo.

* * * * *

UNITED STATES PATENT AND TRADEMARK OFFICE
CERTIFICATE OF CORRECTION

PATENT NO. : 6,964,952 B2
DATED : November 15, 2005
INVENTOR(S) : Park et al.

It is certified that error appears in the above-identified patent and that said Letters Patent is hereby corrected as shown below:

Column 16,
Line 61, replace "acetylphtosphingosine" with -- acetylphytosphingosine --.

Signed and Sealed this

Twenty-fifth Day of April, 2006

JON W. DUDAS
*Director of the United States Patent and Trademark Office*